United States Patent

Minoz et al.

Patent Number: 6,108,571
Date of Patent: Aug. 22, 2000

[54] AMBULATORY RECORDER HAVING A COMMUNICATION WATCHDOG BETWEEN TWO PROCESSORS

[75] Inventors: Alain Minoz, Bromma, Sweden; Thorir Gunnarsson, Reykjavik, Iceland; Malcolm G.S. Williams, Stockholm, Sweden; Arch W. Butler, St. Louis Park, Minn.; Henrik E. Pedersen, Vanloese, Denmark

[73] Assignee: Medtronic, Inc., Minneapolis, Minn.

[21] Appl. No.: 09/237,806

[22] Filed: Jan. 27, 1999

Related U.S. Application Data

[63] Continuation of application No. 09/210,568, Dec. 14, 1998.
[51] Int. Cl.⁷ ............................................. A61B 5/00
[52] U.S. Cl. .......................... 600/361; 600/300; 128/920
[58] Field of Search .................................. 600/300, 361; 128/897–899, 920–925; 364/184–187; 395/180–185.1

[56] References Cited

U.S. PATENT DOCUMENTS

| | | | |
|---|---|---|---|
| 4,892,104 | 1/1990 | Ito et al. | 600/300 |
| 5,645,068 | 7/1997 | Mezack et al. | 600/300 |
| 5,657,759 | 8/1997 | Essen-Moller | 600/300 |
| 5,701,894 | 12/1997 | Cherry et al. | 600/300 |

*Primary Examiner*—Max Hindenburg
*Assistant Examiner*—Michael Astorino
*Attorney, Agent, or Firm*—Thomas F. Woods; Michael J. Jaro; Harold Patton

[57] ABSTRACT

An ambulatory recording system, for medical and especially diagnostic purposes, is described having a communication watchdog between two processors. The two processors may be of differing types. For example, the first processor may be real time processor ("RTP") which handles the sampling function, while the second processor may be a non real time processor ("NRTP") which handles the operating system function. This dual processor design permits relatively low power consumption for data recording (which is handled by the relatively lower power consuming RTP), while also providing a graphical user interface for user simple user operation (which is handled by the relatively higher power consuming NRTP). A communication watchdog between the two processors is provided to reset the device upon the detection of a processor failure or communication failure between the two processors.

16 Claims, 7 Drawing Sheets

AMBULATORY RECORDER HAVING A COMMUNICATION WATCHDOG BETWEEN TWO PROCESSORS

This is a continuation of copending application Ser. No. 08/210,568 filed on Dec. 14, 1998.

FIELD OF THE INVENTION

The present invention relates to ambulatory recording, of medical data especially for diagnostic purposes, and particularly to an ambulatory recorder having a communication watchdog between two processors.

BACKGROUND OF THE INVENTION

Various physiologic signals are often recorded and analyzed. These signals may included digestive pH, various digestive motility and pressure signal, EEG and EMG, to list only a few.

Typically, physicians require the concurrent recording a variety of physiologic signals. For example, gastric pH is often collected at the same time as pressure. Through the concurrent collection of various parameters the physician may better understand the patient's condition.

Ambulatory recording and recorders are widely used to collect such data. Such devices include the Digitrapper Mk III™ ambulatory recorder from Synectics Medical AB, the GastroScan II™ from Medical Instruments Corporation, and the SuperLogger™ from Sandhill Scientific. These types of devices make it possible for patients to remain at home, or at the least be ambulant in a hospital setting while physiological data is recorded. Typically the devices comprise a lightweight recorder in which the desired physiological data signals are temporarily stored and later downloaded for future analysis.

Many types of physiological data may be recorded, including ECG (Electrocardiogram), EEG (Electroencephalogram) or pH and pressure (Motility) in the gastrointestinal tract. Preferably such a recorder should be able to record among a programmable number of channels at a variety of programmable frequencies, while still being small and rugged enough to be used as an ambulatory device.

Such recorders, because they must be ambulatory, are battery powered. Thus an ambulatory medical recorder must minimize energy usage while performing almost constant sampling across a variable number of channels at one or more frequencies. Besides minimizing energy usage, such recorders, however, must also offer robust functionality, i.e., be easy to operate, while also being flexible. Moreover, another crucial requirement is that such recorders be dependable, accurate and reliable.

One approach to construct a recorder offering flexible operation, ease of use, as well as a simple but powerful graphical user interface all while providing dependable, accurate and reliable data sampling and recording is through the use of two processors. This approach may include the use of processor having differing architectures. For example, first processor may be a real time processor ("RTP") which handles the sampling function, while the second processor may be a non real time processor ("NRTP") which handles the operating system function.

Among the problems with a data recorder using two processors is that of communication between the processors. Although this may be a problem regardless of the processors selected, in the situation where the first processor is a RTP and the second processor is a NRTP, the problem is especially acute. In particular, the RTP runs a real time single task software; while the NRTP runs a non-real time multitasking operating system and application with priorities. Thus, communication with the RTP could be started by several tasks within the NRTP at the same time. Ultimately this may lead to confusion in the recorder and ultimately lead to a system failure and/or data loss. While various approaches to coordinating the transfer of data between such processors may be used, there exists a need to provide a reliable but simple method of restarting communication should there be a failure.

SUMMARY OF THE INVENTION

An ambulatory recording, for medical and especially for diagnostic purposes, and particularly to an ambulatory recorder having a communication watchdog between two processors. The two processors may be of differing types. For example, the first processor may be real time processor ("RTP") which handles the sampling function, while the second processor may be a non real time processor ("NRTP") which handles the operating system function. This dual processor design permits relatively low power consumption for data recording (which is handled by the relatively lower power consuming RTP), while also providing a graphical user interface for simple user operation (which is handled by the relatively higher power consuming NRTP). A communication watchdog between the two processors is provided to reset the device upon the detection of a processor failure or communication failure between the two processors.

In particular, the watchdog feature of the present invention is provided in the RTP to restart the NRTP should such a communication or processor failure be detected. Generally, the RTP runs real time single task software and has an internal watchdog which resets the RTP if its real time single task software hangs up. Therefore it is assumed for the recorder that the RTP processor is always alive. The NRTP, in contrast, has a pre-emptive, non-real time multitasking operating system running an application with several tasks. Therefore the latency time for the NRTP to respond to the RTP cannot be specified with accuracy. Some tasks of the NRTP can hang up or be deleted without making the whole system looking dead. For example, the user interface could still work properly but the task that gets and saves the samples into non-volatile memory could be stopped. This cannot be allowed to occur since the primary purpose of this device is to measure and save safely physiologic values. For such reasons a simple "time-out" approach will not always be guaranteed to perform acceptably.

The present invention provides a watchdog function for the NRTP and the NRTP to RTP communication link by resetting the NRTP processor if a communication failure is detected. In particular, the present invention permits the RTP to reset the NRTP if a communication failure is detected. In addition, the present invention also permits the RTP to do a simple communication to test that the NRTP is responding. Furthermore, the watchdog of the present invention also causes the RTP to reset itself if the task it performs hangs up. In this manner the device ensures that the samples sampled by the RTP may be processed through the NRTP and thus reliably recorded.

BRIEF DESCRIPTION OF THE DRAWINGS

The FIGS. are not necessarily to scale.

DETAILED DESCRIPTION OF THE DRAWINGS

Figure 1A:
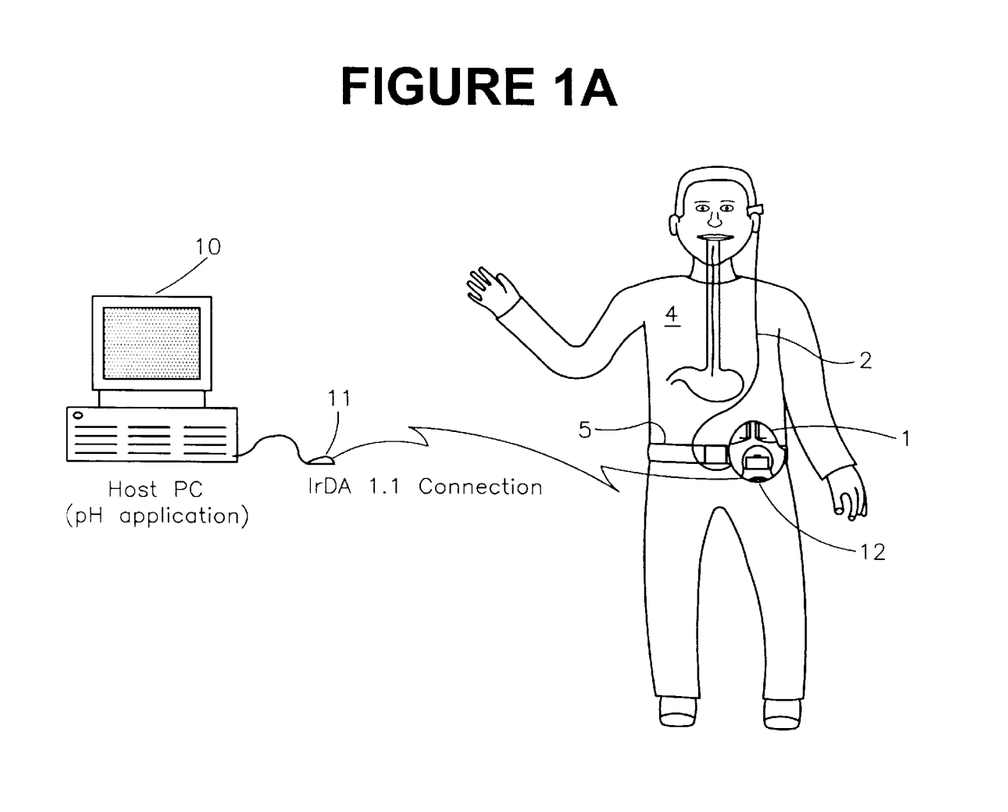
FIG. 1A depicts an ambulatory recorder of the present invention.

FIG. 1A depicts an ambulatory recorder of the present invention. As seen, ambulatory recorder 1 of the present invention may be carried by a patient. In the preferred embodiment, the recorder may be either carried through a mounting in the back which fastens to a patient's belt 5, or the same mounting may be coupled to be carried using a shoulder harness (not shown). As seen, recorder is coupled to the patient 4 through one or more sensing catheters 2. Sensing catheters may be positioned in any area of the patient's body, from which data is to be sensed, including the esophagus, as depicted in this figure. It should be noted that the ambulatory recorder of the present invention may be used to collect many or various types of data including gastrointestinal, neurological, as well as neuromuscular, EEG or EMG data.

Among the various sensing catheters which may be coupled to the device are manometry catheters and pH testing catheters, including the Synectics Medical AB, Stockholm, Sweden Model G 91-9 series of Multi use pH catheters; Synectics Medical AB Model G 91-2 series of Multi use pH catheters with perfusion port; or the Zinectics Inc., Salt Lake City, Utah disposable 24 pH catheter Model series G91-6 or G 91-7. While a single catheter 2 is shown depicted in this figure, recorder further permits two separate sensors to be coupled to the device, as seen in FIG. 1B.

As further seen in FIG. 1A, the recorder may also communicate with a host PC 10 via an infra red data link facility through an IrDA connection 11, for example, a JETEYE ESI-57680 available form Extended Systems, Inc., Boise, Id., which connects with the recorder using the infra Red Data Association 1.1 Connection Protocol. As seen, infra red data connection makes a link to infra red port 12 on recorder.

Figure 1B:
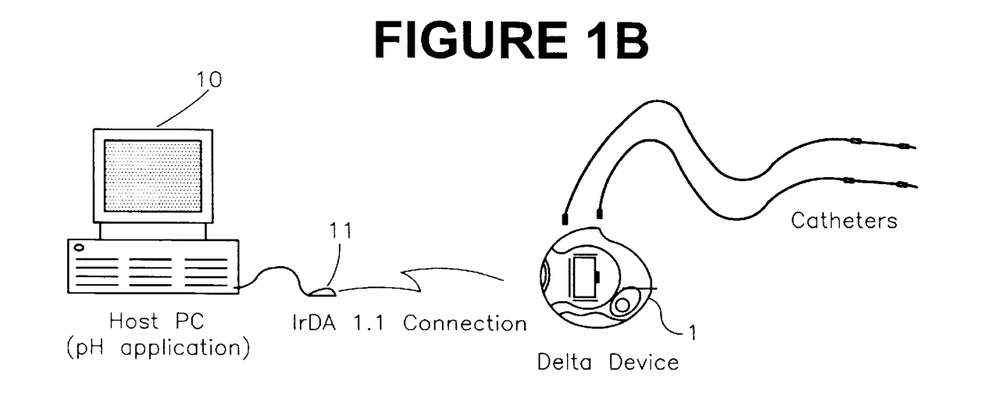
FIG. 1B illustrates a further manner in which the recorder 1 may also have an infra red data communication link made with a host PC.

FIG. 1B illustrates a further manner in which the recorder 1 may also have an infra red data communication link made with a host PC. In particular, the infra red data communication data recorder may be further made when the recorder is not worn by the patient. As discussed in more detail below, one of the advantages of the present invention is that the infra red data components and recorder case permits such a link to be made when the device is worn as shown in FIG. 1A as well as if the device is merely removed from the patient and positioned in proximity to mouse 11.

Figure 1C:
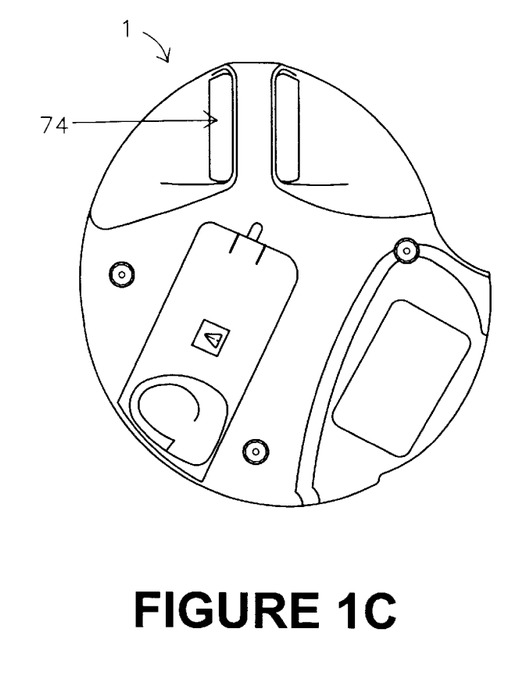
FIG. 1C is a back view of the recorder shown in FIGS. 1A and 1B.

FIG. 1C is a back view of the recorder shown in FIGS. 1A and 1B. As seen, recorder 1 features a belt loop 74 which may be used to mount the recorder to a patient using either the patient's belt or the shoulder strap.

Figure 1D:
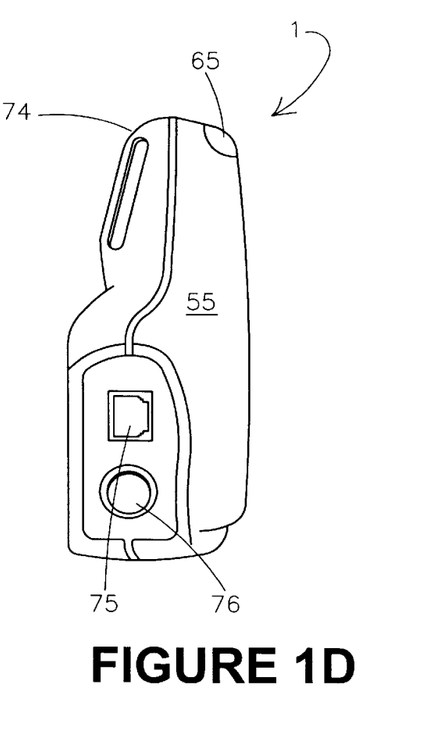
FIG. 1D is a side view of recorder 1 shown in FIGS. 1A and 1B.

FIG. 1D is a side view of recorder 1 shown in FIGS. 1A and 1B. As further seen in this view, housing 55 features a pair of sensor inputs 75 and 76. In the preferred embodiment, input 75 is for a pH catheter while input 76 is for a pressure measuring catheter.

Figure 2:
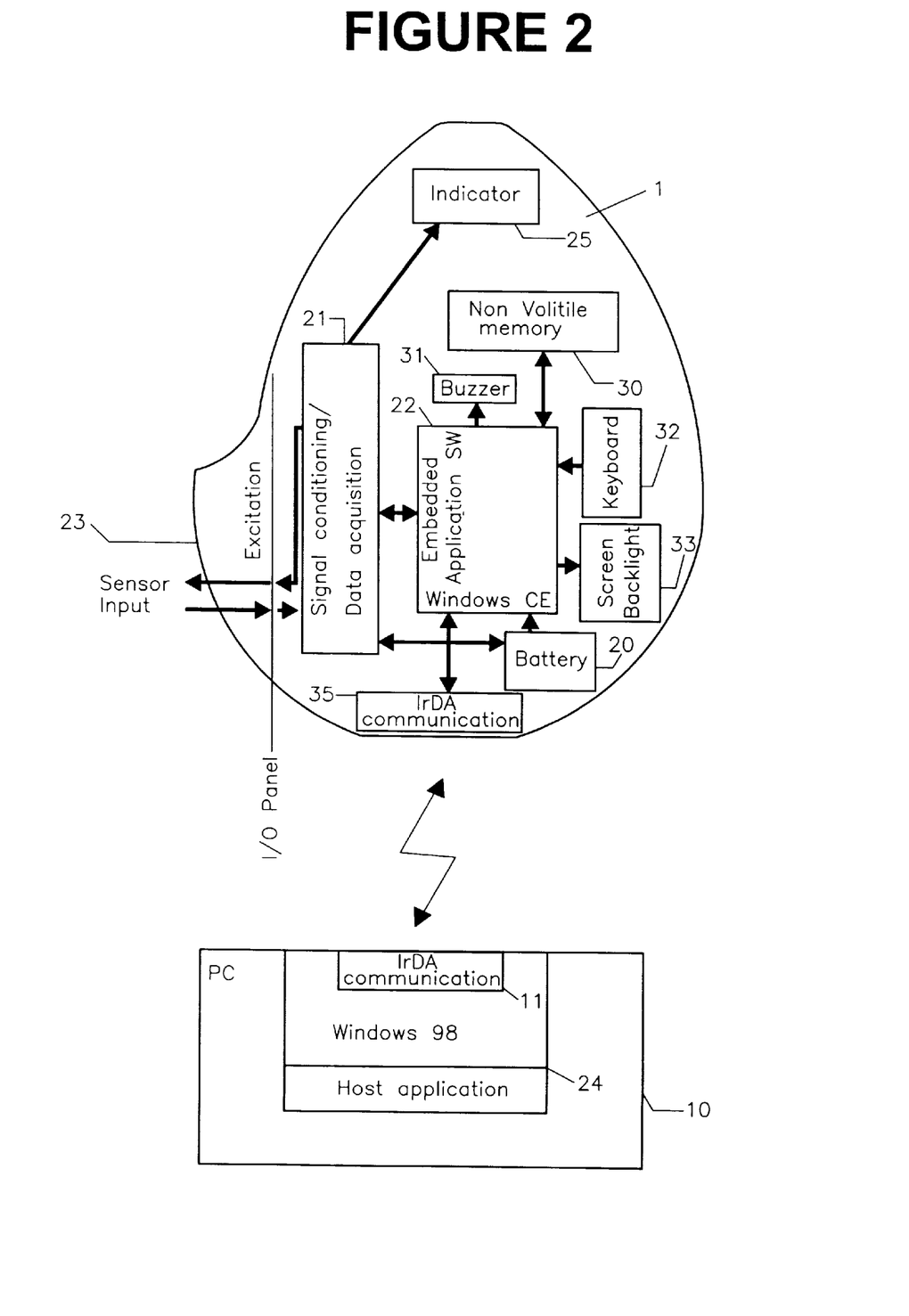
FIG. 2 is a block diagram of the data recording system shown in FIG. 1B.

FIG. 2 is a block diagram of the data recording system shown in FIG. 1B. As seen, recorder 1 features a battery 20 which is coupled to the signal conditioning/data acquisition block that is driven by a real time processor 21, the battery is coupled as well as to a non-real time processor 22 that runs the application. As disclosed in more detail below, real time processor 21 is a lower power processor which is used to sample data which is received from sensor input 23 by a sensor attached thereto (not shown in this FIG.).

Sampling is achieved through the signal conditioning providing an excitation to the sensor coupled to sensor input 23. Such excitation voltage is often used to power and, thus, permit sensing to occur in a variety of different types of sensors, including pressure sensors, as is well known in the art. The sampling and sensing controls are provided by the real time processor 21. Real time processor also drives a LED indicator 25 to show the system is running even when the screen is off.

As further seen, this processor is coupled to second non-real time processor 22. Second processor 22 is provided primarily to perform those high processing operations associated with multitasking, graphical user interface, floating point calculation, Infra Red communication and long term memory storage. In particular, second processor is primarily provided to operate a Windows CE operating system as well as one or more embedded applications, as depicted. As further seen, this processor is coupled to audible buzzer 31 as well as keyboard controls 32, a screen 33 and non-volatile memory 30. Non-volatile memory provides a long term memory for the device such that data can be recorded and preserved even if power is lost. In the preferred embodiment, keyboard controls processes a series of four push buttons, each of which provide one or more different types of system inputs, as provided by the Windows CE™ operating system, available from Microsoft Corporation, Redmond, Wash.

As further seen in this figure, recorder features an infra red port 35 to communicate with the host PC. As depicted in FIG. 1B, the infra red connection permits the recorder 1 to receive and exchange data with host PC 10. Host PC, as seen, includes both a Windows 98™ operating system available from Microsoft Corporation, Redmond, Wash., as well as one or more host applications. Host applications permit the treatment of the recorded values and help for diagnostic.

In the preferred embodiment the real time processor ("RTP") is the model PIC16LC67 from Microchip Technology Inc., Chandler, Ariz.; the non real time processor ("NRTP") is the model ElanSC400 from Advanced Micro Devices, Inc. Sunnyvale, Calif.; and non-volatile memory is the model Minicard AMMCL004AWP from Advanced Micro Devices, Inc. Sunnyvale, Calif.

Figure 3:
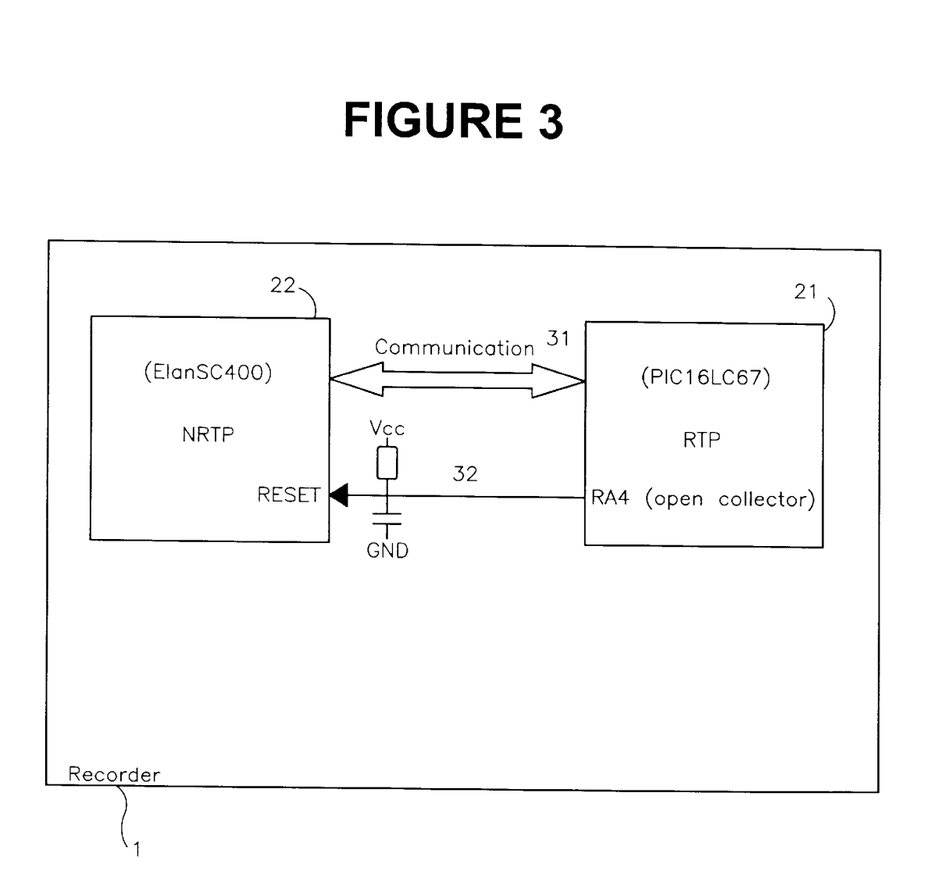
FIG. 3 represents in more detail the communication lines between the RTP 21 and the NRTP 22 used in the recorder 1.

FIG. 3 represents in more detail the communication lines between the RTP 21 and the NRTP 22 used in the recorder 1. The two processors need to exchanges data (i.e. to setup a recording or download samples) via a communication one or more lines, represented here generally as bus 31. While a single bus is depicted any number of possible configurations may be used for inter processor communication, including a single bus, a series of lines or a blend of both. During communication the validity of the data and the proper response of the NRTP are checked through a synchronization protocol, generally consisting of a combination of a time out and read back of data. The preferred synchronization protocol for the present invention may be seen in the patent application of the same inventors filed on this same day and entitled "Ambulatory Recorder Having Synchronized Communication Between Two Processors" (our ref. P-8142 CIP #1) If, during communication between the NRTP and the RTP a failure is detected, then the RTP retries the communication. Such a retry at the communication may be attempted a pre-selected number of times. If it fails repeatedly, then the RTP resets the NRTP via reset line 32.

Generally speaking, the ambulatory recorder 1 has two modes. During the non-recording mode the user may set the recording parameters. During the recording mode the recorder actually records. In either mode communication may fail and the watchdog feature of the present invention may be utilized to thereafter reset the recorder. The two modes, communication failure and recorder reset are discussed in more detail below.

Figure 4:
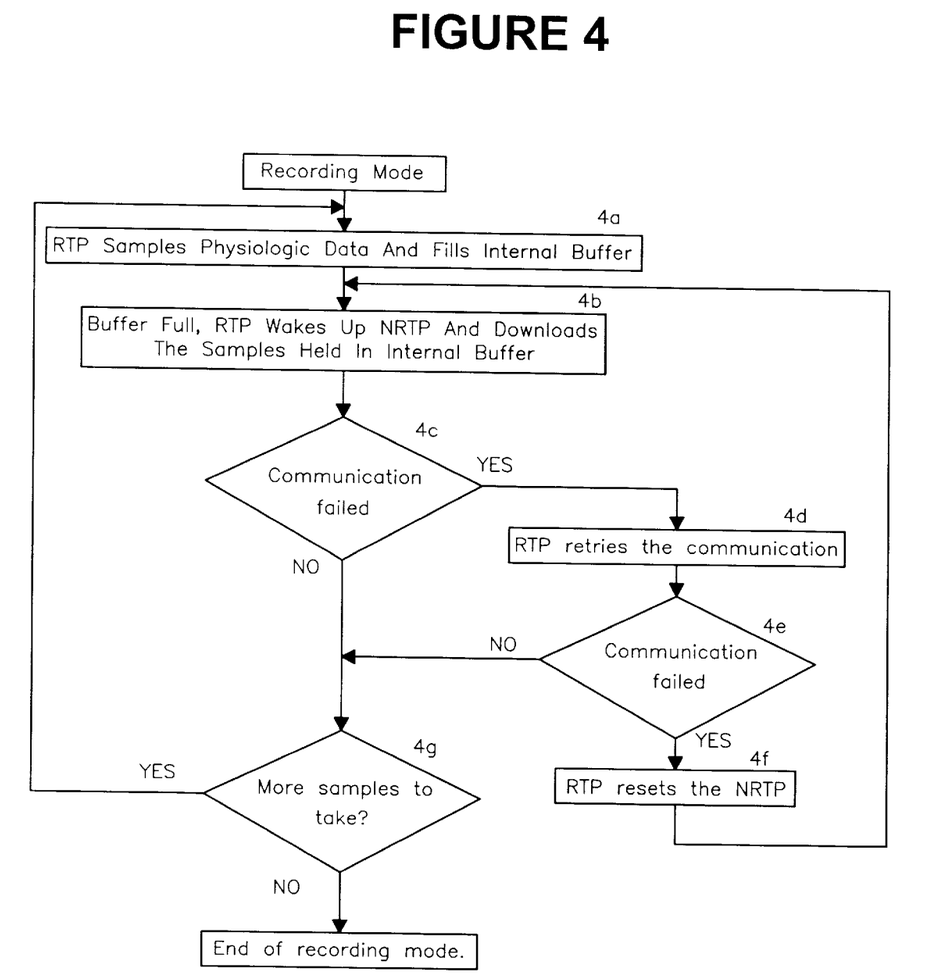
FIG. 4 depicts the step used by the recorder in the recording mode.

FIG. 4 depicts the step used by the recorder in the recording mode. At step 4a RTP 21 samples physiologic data and fills its internal buffer. NRTP 22, in the meantime, sits in a very low power mode. At step 4b, when the internal buffer or RTP 21 is full, the RTP 21 wakes up NRTP 22 and downloads the samples to be saved to the non-volatile memory. If a communication failure happens during the transfer, as depicted at step 4c, then RTP 21 retries the communication several times, as depicted at step 4d. The exact number of retries of communication may be programmed or pre-selected, such as five. If the communication fails again, then this means NRTP 22 will not be able to save the samples, as depicted at step 4e. RTP 21 resets NRTP 22, as depicted at step 4f. If the communication did not fail in step 4c, then this indicates the samples could be and indeed were downloaded and saved properly. Such a transfer of data will continue as needed until the end of recording is reached, as depicted at step 4g. In the preferred embodiment the communication failure is detected according to the teachings of the patent application of the same inventors filed on this same day and entitled "Ambulatory Recorder Having Synchronized Communication Between Two Processors" (our ref. P-8142 CIP #1).

Figure 5:
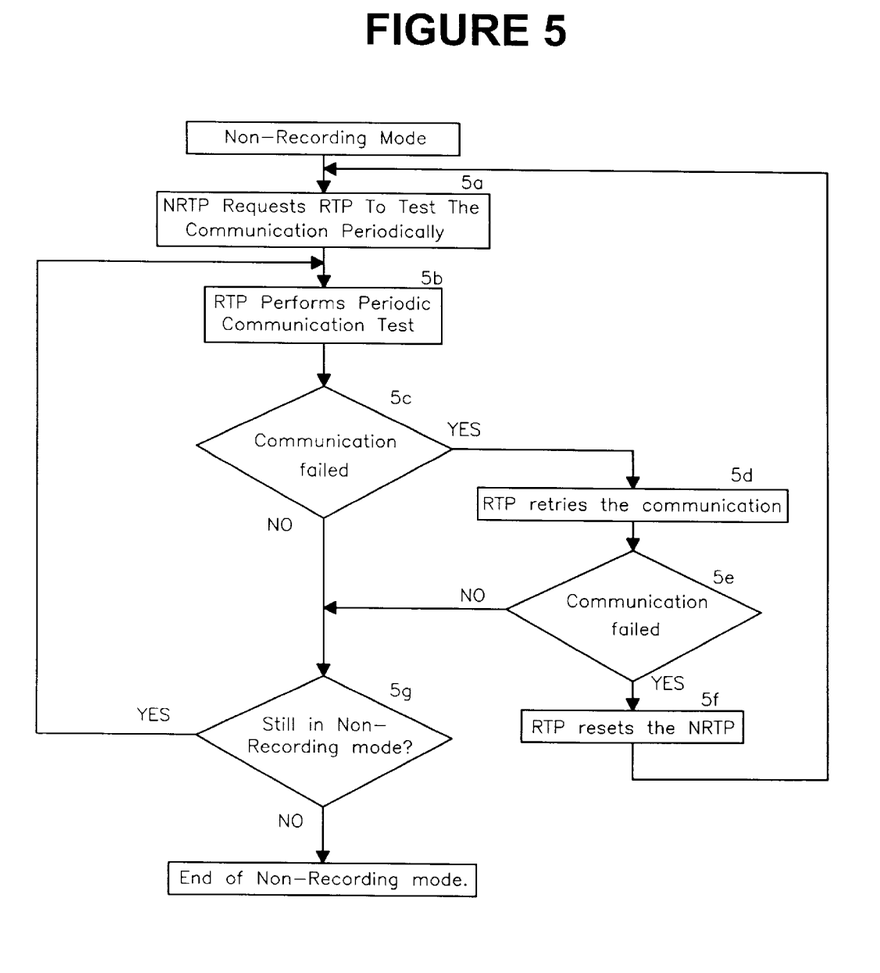
FIG. 5 depicts the step used by the recorder in the non-recording mode.

FIG. 5 depicts the step used by the recorder in the non-recording mode. First, including upon device boot up, NRTP 22 requests RTP 21 to test the communication periodically (one minute, for example) as depicted at step 5a. The particular period may be pre- selected or programmed. RTP 21 will thereafter perform a simple communication as programmed (every minute, for example) to will test whether NRTP 22 is responding, as depicted at step 5b. Through this periodic test, any hanging up of NRTP will be readily detected by RTP so that the NRTP may be rebooted. This, then, permits the period during which data could be lost to be minimized If a communication failure is happens, as depicted at step 5c, then RTP 21 retries the communication several times as depicted at step 5d. If the communication fails again it means that the NRTP 22 is not running properly, as depicted at step 5e. RTP 21 resets NRTP 22 as depicted at step 5f. This is further illustrated in FIG. 6. In the preferred embodiment the communication failure is detected according to the teachings of the patent application of the same inventors filed on this same day and entitled "Ambulatory Recorder Having Synchronized Communication Between Two Processors" (our ref. P-8142 CIP #1). If the communication did not fail in step 5c, then this indicates that NRTP 22 is running properly. This will continue until they enter in the recording mode as seen at step 5g.

Figure 6:
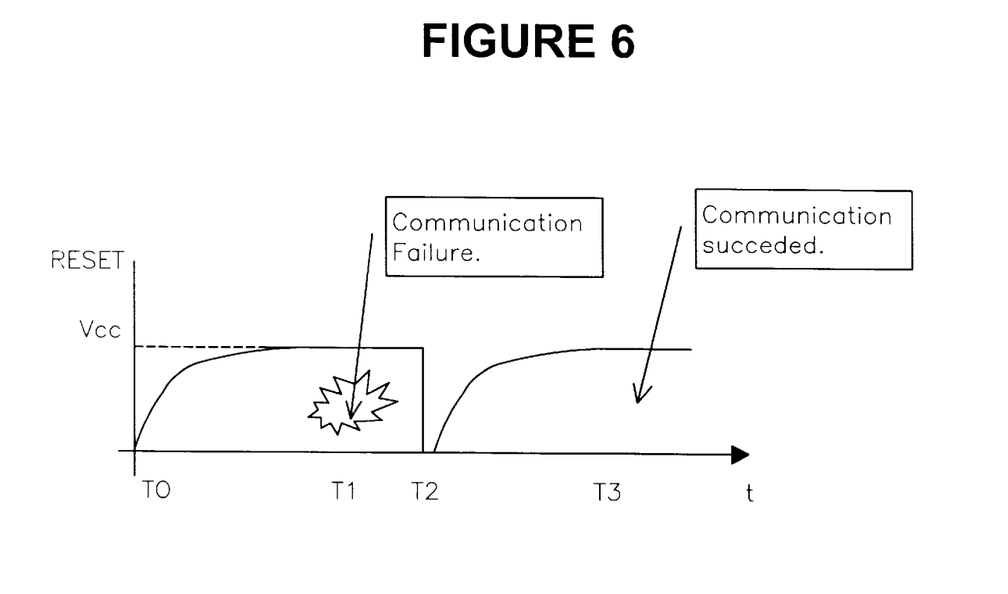
FIG. 6 depicts the state of the reset line.

FIG. 6 shows the voltage on the reset line (32 in FIG. 3). NRTP (22 in FIG. 3) internally resets when the voltage on the reset line is 0 and restart when the voltage on the reset line is Vcc (Vcc the voltage applied to the processor). Referring no directly to FIG. 5, at time T0, the NRTP is reset, and the capacitor on the reset line will charge up to Vcc. When the voltage on the reset line reaches Vcc, the NRTP begins to operate or starts. At time T1, a communication failure is shown as happening, and, as described above, the RTP 21 would retries the same communication a preset number of times. If the failure continues to persist, at a time T2 the RTP 21 resets the NRTP by forcing the Reset line to zero (0) Volts. This may be accomplished by discharging the capacitor for a short period. The capacitor on the reset line will charge again at Vcc and when the voltage on the reset line reaches Vcc, the NRTP again restarts. The RTP 21 will again retry to communicate, shown here as at time T3. As also shown, at this time the communication is successful and the samples may thereafter saved to non volatile memory. Although not shown in this FIG., the watchdog feature of the present invention may also cause the RTP to reset itself if the task it performs hangs Such a reset of the RTP may cause a loss of data. This loss, however, is not important since if the RTP is hung, the data collected may be either not valid, or inaccessible, or both. Moreover, watchdog in the RTP preferably has a period of 2.3 seconds which means that it will detect a RTP failure at least in 2.3 seconds. That is pretty fast compared to a typical sampling period (1/Hz). Thus, the fact that the watchdog may be used to also reset the RTP is of not great consequence to the loss of actual and valid data.

Thus, the present invention concerns an ambulatory recording device and system for medical and especially diagnostic purposes, and an ambulatory recorder device and system having a communication watchdog between two processors. The recorder preferably features two processors which are of differing architecture—the first processor being a real time processor which handles the sampling function, while the second processor being a non real time processor which handles the operating system function. It should be understood, however, that while two different types of processors are illustrated, the invention may also be used with two identical processors, such as two real time processors. Further, the invention may also be used within a single mixed signal processor, if desired as well as in a recorder featuring three or more processors. It is contemplated that various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. An ambulatory medical recording system comprising:
    a medical sensing catheter;
    a medical data recorder coupled with the medical sensing catheter, the medical data recorder comprising:
    a first processor and a second processor, the fist and second processors communicating along a first line, the first processor comprising means for sensing a communication failure between the first processor and the second processor, the first processor further comprising means for resetting the second processor in response to sensing the communication failure.

2. An ambulatory medical recording system according to claim 1 wherein the first processor is a real time processor RTP.

3. An ambulatory medical recording system according to claim 2 wherein the second processor is a non real-time processor NRTP.

4. An ambulatory medical recording system according to claim 1 wherein the first processor and the second processor communicate along the first communication line and a second communication line.

5. An ambulatory medical recording system according to claim 1 wherein the first line comprises a data bus.

6. An ambulatory medical recording system according to claim 1 further comprising the second processor having means for directing the first processor to periodically perform a test communication with the second processor.

7. An ambulatory medical recording system according to claim 1 wherein the means for resetting the second processor comprises a reset line coupled between the first processor and the second processor, the reset line controlled by the first processor, the reset line permitting the first processor to reset the second processor.

8. An ambulatory medical recording system according to claim 6, wherein the means for periodically performing a test communication with the second processor further comprises means for sensing whether the test communication has failed and repeating the test communication a pre-selected number of times.

9. An ambulatory medical recording system according to claim 8, wherein the means for resetting the second processor is activated upon the repeating of the test communication a pre-selected number of times.

10. An ambulatory medical recording system according to claim 1 further comprising a non-volatile memory coupled to the second processor.

11. An ambulatory medical recording system according to claim 1 further comprising means for infra red data communication coupled to the second processor.

12. An ambulatory medical recording system according to claim 1 further comprising the first processor having means for periodically performing a test communication with the second processor.

13. An ambulatory medical recording system according to claim 12, wherein the first processor has means for resetting the second processor.

14. An ambulatory medical recording system according to claim 13, wherein the means for resetting the second processor comprises a reset line coupled between the first processor and the second processor, the reset line controlled by the first processor, the reset line permitting the first processor to reset the second processor.

15. An ambulatory medical recording system according to claim 14, wherein the means for periodically performing a test communication with the second processor further comprises means for sensing whether the test communication has failed and repeating the test communication a pre-selected number of times.

16. An ambulatory medical recording system according to claim 15, wherein the means for resetting the second processor is activated upon the repeating of the test communication the pre-selected number of times.

* * * * *

UNITED STATES PATENT AND TRADEMARK OFFICE
CERTIFICATE OF CORRECTION

PATENT NO.   : 6,108,571
DATED        : August 22, 2000
INVENTOR(S)  : Minoz et al.

It is certified that error appears in the above-identified patent and that said Letters Patent is hereby corrected as shown below:

<u>Title page,</u>
Item [57], ABSTRACT,
Line 1, change "recording system, for" to -- recording system for --.

<u>Column 6,</u>
Line 58 change "the fist and" to -- the first and --.

<u>Column 7,</u>
Line 21, change "claim 6," to -- claim 1, --.

Signed and Sealed this

Third Day of June, 2003

JAMES E. ROGAN
*Director of the United States Patent and Trademark Office*